United States Patent [19]

Fauss

[11] 4,405,803

[45] Sep. 20, 1983

[54] PROCESS FOR THE PREPARATION OF SILYLISOCYANATES

[75] Inventor: Rudolf Fauss, Cologne, Fed. Rep. of Germany

[73] Assignee: Bayer Aktiengesellschaft, Leverkusen, Fed. Rep. of Germany

[21] Appl. No.: 380,581

[22] Filed: May 21, 1982

[30] Foreign Application Priority Data

Jun. 3, 1981 [DE] Fed. Rep. of Germany ........ 3122014

[51] Int. Cl.³ .............................................. C07F 7/10
[52] U.S. Cl. .................................................... 556/410
[58] Field of Search ......................................... 556/410

[56] References Cited

U.S. PATENT DOCUMENTS

| | | | |
|---|---|---|---|
| 2,559,340 | 7/1951 | Bluestein | 260/448.2 |
| 3,053,871 | 9/1962 | Aries | 556/410 X |
| 4,176,131 | 11/1979 | Shih et al. | 260/448.2 |

FOREIGN PATENT DOCUMENTS

| | | | |
|---|---|---|---|
| 1162367 | 2/1964 | Fed. Rep. of Germany | 556/410 UX |
| 1965741 | 7/1971 | Fed. Rep. of Germany | 556/410 UX |
| 55-102589 | 8/1980 | Japan | 556/410 |

OTHER PUBLICATIONS

Houben-Weyl, Methoden der Organischen Chemie 13/5, p. 126 et seq., (1979).

Journal of American Chemical Society, vol. 72, p. 3045, (1950).

J. Goubeau and D. Paulin, Darstellung von Methylsilicuimisocyanaten, Ber. 93, 1111, (1960).

*Primary Examiner*—Paul F. Shaver
*Attorney, Agent, or Firm*—Gene Harsh; Joseph C. Gil; Lyndanne M. Whalen

[57] ABSTRACT

This invention relates to a process for the preparation of silylisocyanates corresponding to the formula:

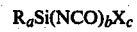

$$R_aSi(NCO)_bX_c$$

wherein
R denotes a hydrocarbon group,
X denotes chlorine or bromine,
a represents an integer of from 1 to 3,
b represents an integer of from 1 to 3, and
c represents an integer of from 0 to 2 and the sum of $a+b+c=4$.

These silylisocyanates are produced by reacting halogen silanes corresponding to the formula:

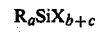

$$R_aSiX_{b+c}$$

with urea at atmospheric pressure in a polar solvent at a temperature of at least 100° C.

4 Claims, No Drawings

PROCESS FOR THE PREPARATION OF SILYLISOCYANATES

BACKGROUND OF THE INVENTION

This invention relates to a process for the preparation of silylisocyanates.

Various methods for the preparation of silylisocyanates are known (see, e.g., Houben Weyl, 13/5, page 126 et seq (1979)). According to German Offenlegungsschrift No. 1,965,741, silylisocyanates may be prepared by reacting silylhalides with salts of cyanic acid. Methods employing urea instead of cyanic acid salts have been investigated by J. Goubeau and D. Paulin (see Ber. 93, 111 (1960)). Since urea is not split to give off isocyanic acid until it reaches a temperature of about 130° C. and silylchlorides are already gaseous at this temperature at atmospheric pressure, Goubeau and Paulin were forced to carry out the synthesis reaction under pressure. They found that the reaction of trimethyl silylchloride with urea started at 240° C. and that a maximum yield of trimethyl silylisocyanate (amounting to 65-75% of the theoretical yield) was obtained within 4 to 5 hours if the reaction was carried out at 300°±20° C. However, reaction of dimethyl silyldichloride with urea yielded at most 5-10% of the theoretical yield of dimethyl silyldiisocyanate and substantial quantities of [(CH₃)₂SiO]₃ and [(CH₃)₂SiO]₄ as well as biuret, ammonium cyanate, cyanuric acid and tricyanile urea as by-products. A considerable proportion of the starting compounds therefore reacted to form by-products which could not be recycled.

SUMMARY OF THE INVENTION

It is an object of the present invention to provide a process for the production of silylisocyanates.

It is also an object of the present invention to provide a process for the production of silylisocyanates in high yield which process may be carried out at atmospheric pressure.

It is a further object of the present invention to provide a process for the production of silylisocyanates from silanes containing at least one halogen atoms.

It is yet another object of the present invention to provide a process for the production of silylisocyanates from silanes containing at least two halogen atoms in which the halogen atoms may be substituted stepwise by isocyanate groups.

These and other objects which will be apparent to those skilled in the art are accomplished by reacting a halogen silane corresponding to a specified formula with urea in a polar solvent at a temperature greater than or equal to 100° C. and atmospheric pressure.

DETAILED DESCRIPTION OF THE INVENTION

The present invention relates to a process for the preparation of silylisocyanates corresponding to the general formula:

$$R_aSi(NCO)_bX_c$$

wherein

R represents an aliphatic hydrocarbon group having a total of 1 to 18 carbon atoms which group is optionally olefinically unsaturated and optionally contains inert substituent(s); an aromatic hydrocarbon group having a total of 6 to 18 carbon atoms optionally containing inert substituent(s); an araliphatic hydrocarbon group having a total of 7 to 18 carbon atoms optionally containing inert substituent(s); a cycloaliphatic hydrocarbon group having a total of 5 to 18 carbon atoms optionally containing inert substituent(s); an alkoxy group having 1 to 18 carbon atoms; or an aryloxy group having 6 to 18 carbon atoms;

X represents chlorine or bromine, a represents an integer of from 1 to 3, b represents an integer of from 1 to 3, and c represents an integer of from 0 to 2, and the sum of a+b+c is 4. In this process, halogen silanes corresponding to the general formula:

$$R_aSiX_{b+c}$$

(in which the substituents and subscripts have the same meaning as given above) are reacted with urea in a polar solvent at a temperature of at least 100° C. Application of external pressure to the reaction mixture is unnecessary.

Any halogen silane corresponding to the general formula may be used as a starting material in the process of the present invention. Halogen silanes in which "R" represents a saturated aliphatic hydrocarbon group having 1 to 4 carbon atoms (particularly a methyl group) and "X" represents chlorine are preferred.

The following are examples of suitable halogen silanes: methyl silyltrichloride, dimethyl silyldichloride, trimethyl silylchloride, dimethyl silyldibromide, di-n-butyl-silyldichloride, distearylsilyldichloride, dicyclohexyl-silyldichloride, phenyl-silyltrichloride, benzyl-silyltrichloride and dimethyl-ethyl-silylchloride.

The starting material to be reacted with the halogen silanes exemplified above is urea.

The reaction between the halogen silanes and urea is carried out in the presence of a polar solvent or of solvent mixtures consisting substantially of polar solvents. The solvent or solvent mixtures should have a boiling point at atmospheric pressure of at least 110° C., preferably at least 140° C. and most preferably at least 190° C. Sulfolane and/or organic acid amides which are liquid under the reaction conditions, such as dimethyl formamide, dimethyl acetamide, N-methyl pyrrolidone, tetramethyl urea, tetraethyl urea and/or ε-caprolactam are particularly suitable solvents. The solvent or solvent mixture should be one in which urea may be readily dissolved in order to eliminate unwanted side reactions, particularly the formation of cyanuric acid.

In the process of the present invention, the reactants are used in quantities such that from 0.8 to 2 mol (preferably 1 to 1.5 mol) of urea are present for each mol of halogen bound in the halogen silane if complete replacement of the halogen substituents by the isocyanate substituents is desired. If silanes containing both isocyanate groups and halogen substituents are to be prepared from halogen silanes containing several halogen atoms, it is advisable to use from 0.8 to 1.2 mol (preferably 1 mol) of urea for each mol of halogen which is to be substituted by an isocyanate group.

The reaction of the present invention is carried out in the temperature range from 100° C. to 200° C., preferably from 130° C. to 160° C.

The process of the present invention is generally carried out by first introducing the urea dissolved in solvent into the reaction vessel, preheating the solution to about 100°–120° C., adding the halogen silanes (with vigorous mixing) and further raising the reaction temperature. The silylisocyanate formed is preferably continuously removed from the reaction vessel by distillation and then fractionated. Any unreacted halogen silanes obtained may be reused. Towards the end of the reaction, it is advisable to raise the sump temperature sharply (e.g., to 180° C.) in order to expel the silylisocyanates as completely as possible.

When using sulfolane, it may be advisable (e.g., for preparing trimethyl isocyanate) to expel the isocyanate quantitatively towards the end of the reaction with a lower boiling auxiliary solvent (e.g., toluene) at a sump temperature of 170° C.

When preparing methyl triisocyanatosilane, the end product must be removed from the reaction mixture by application of a vacuum after the reaction has been completed.

The best method for removing the products (by distillation) is dependent upon the boiling point of the product and upon the solvent(s) used. The optimum conditions may, however, be determined by a simple preliminary test. When preparing high boiling products, it is preferred to use comparatively low boiling solvents such as dimethyl formamide or N-methyl pyrrolidone. In such cases, working up of the reaction mixture may advantageously be carried out by adding a non-polar solvent (such as toluene, xylene, cleaning petrol or chlorobenzene) to the reaction mixture to precipitate by-products, particularly any ammonium halides formed. The filtrate freed from these precipitates may then be worked up by evaporating off the solvent. The end products are obtained as distillation residue.

The preparation of isocyanatosilanes containing halogen substituents (for example, the preparation of dimethyl chloroisocyanatosilane from dimethyl dichlorosilane) may be carried out by rapidly pumping about one mol of dichlorodimethyl silane at about 140° C. into a solution of one mol of urea in sulfolane and continuously distilling off the product mixture. This mixture includes dimethyl chloroisocyanatosilane formed as main product and unreacted dimethyl dichlorosilane and dimethyl diisocyanatosilane. If the formation of dimethyl diisocyanatosilane is to be substantially suppressed, it is advisable to use the dichlorodimethyl silane in excess (based on the quantity of urea).

The process of the present invention is generally carried out using 4–10 molar solutions (preferably 6–8 molar solutions) of urea in the above-mentioned solvents. The solvents may be recovered by distillation after the reaction mixtures have been worked up by distillation. Before recovering the solvent by distillation, any ammonium halides formed may be removed by filtration and washed out using an apolar solvent such as toluene.

The halogen-free isocyanatosilanes obtained as products of the process of the present invention are valuable intermediate products for organic syntheses. They are useful, for example, in the preparation of acyl isocyanates from organic acid chlorides as described, for example, in Soviet Union Pat. No. 498,290. Such acyl isocyanates are valuable dehydrating agents for pigments in lacquers sensitive to moisture. The halogen-substituted isocyanatosilanes obtained as products of the process of the present invention may also be used as polymer additives in hydraulic liquids or in dielectric materials.

Having thus described my invention, the following examples are given by way of illustration. The percentages given in these examples are percentages by weight, unless otherwise indicated.

EXAMPLES

EXAMPLE 1

210 g (3.5 mol) of urea were heated in 400 ml of sulfolane and as the sump temperature rose, 759 g (7 mol) of trimethyl silylchloride were introduced into the sump phase over a period of 3 hours, starting at a sump temperature of about 110° C. The temperature of the solution was gradually raised to about 145° C. Trimethyl silylisocyanate and unreacted trimethyl silylchloride were removed by way of an attached reflux condenser heated to 100° C. When all the trimethyl silylchloride had been added, the temperature was briefly raised to 180° C. 733 g of distillate were obtained. According to gas chromatographic determination, this distillate was made up of 48.6% of trimethyl silylchloride and 51.4% of trimethyl silylisocyanate.

370 ml sulfolane were recovered from the sump by suction filtration of the precipitated ammonium chloride.

EXAMPLE 2

120 g (2 mol) of urea were added to 500 ml of N-methyl pyrrolidone and the mixture was heated. From 100° C. upward, 271 g (2.5 mol) of trimethyl silylchloride were slowly pumped into the sump phase. The temperature was maintained at 140°–150° C. Trimethyl silylisocyanate and unreacted trimethyl silylchloride were distilled over into a receiver by way of a reflux condenser heated to 100° C. Trimethyl silylchloride was distilled from this receiver through a packed column (60 cm). The trimethyl silylchloride thus recovered was returned to the reaction vessel. The cycle was stopped when no more trimethyl silylisocyanate was formed. The end point of the reaction was readily seen from the stationary equilibrium established in the separation of silylchloride/silylisocyanate. 172 g of trimethyl silylisocyanate (Boiling point 91° C.) were isolated after fractional distillation.

EXAMPLE 3

The procedure was the same as in Example 2 with the exception that 450 ml of dimethyl formamide were used as solvent. According to gas chromatographic analysis, the sump phase of the silylchloride/silylisocyanate separation contained 200 g of trimethyl silylisocyanate.

EXAMPLE 4

189 g (3.15 mol) of urea were heated in 600 ml of N-methyl pyrrolidone and from 100° C. upward 325 g (3 mol) of trimethyl silylchloride were slowly pumped in. Unreacted trimethyl silylchloride was returned to the reaction vessel by the method described in Example 2. Towards the end of the reaction, the reused trimethyl silylchloride already contained some trimethyl silylisocyante. After completion of the reaction, the sump phase was heated to the reflux point of N-methyl pyrrolidone to expel the silyl compounds quantitatively.

320 g of reaction product were isolated. This product was determined by gas chromatography to contain 288 g of trimethyl silylisocyanate and 28 g of trimethyl silylchloride.

EXAMPLE 5

420 g (7 mol) of urea and 1200 ml of sulfolane were heated to 100° C. and the temperature was slowly raised to 180° C. while 677 g (5.25 mol) of dimethyl dichlorosilane were introduced. Unreacted starting material and the reaction products formed were removed by way of a reflux condenser heated to 180° C. After the reaction was complete, the receiving vessel contained 530.4 g of liquid which was determined by gas chromatography to contain 21% of dimethyl dichlorosilane, 30.3% of dimethyl chloroisocyanatosilane and 46% of dimethyl diisocyanatosilane. The last two products were identified by GC/MS coupling. The following boiling points were obtained when the reaction product was redistilled.

Dimethyl chloroisocyanatosilane 103°–105° C.; and
Dimethyl diisocyanatosilane 135°–137° C.

EXAMPLE 6

120 g (2 mol) of urea were heated in 500 ml of sulfolane and when the temperature reached 120° C., 258 g (2 mol) of dichlorodimethyl silane were pumped in over a period of 1.5 hours. The sump temperature was raised to 140° C. and unreacted starting material and end products were removed by way of a reflux condenser heated to 145° C. The sump temperature was briefly raised to 180° C. towards the end of the reaction. Analysis by gas chromatography showed that the 221 g of distillate collected contained 21.7% of dimethyl dichlorosilane, 44.4% of dimethyl chloroisocyanatosilane and 29.2% of dimethyl diisocyanatosilane.

EXAMPLE 7

150 g (1 mol) of methyl trichlorosilane were introduced into a solution of 180 g (3 mol) of urea and 500 ml of sulfolane at temperatures starting from 110° C. The reaction was exothermic and the reaction temperatures rose to 150° C. 60 g of a colorless liquid was distilled off at 58°–67° C. under a water jet vacuum. GC/MS coupling showed that the liquid was a mixture of about 30% methyl chlorodiisocyanatosilane and about 70% methyl triisocyanatosilane.

EXAMPLE 8

60 g (1 mol) of urea in 400 ml of sulfolane were heated to 130° C. and 168.5 g (1 mol) of diethoxy methyl silylchloride were pumped in within 30 minutes. The sump temperature was raised to 145° C. during the pumping.

The volatile constituents were then distilled off under vacuum (14 torr) up to a sump temperature of 130° C. and the distillate was then redistilled. 100 g of diethoxymethyl silylisocyanate (boiling point 149° C.) were obtained.

What is claimed is:

1. A process for the production of a silylisocyanate of the formula $$R_a Si(NCO)_b X_c$$

wherein

R represents an aliphatic hydrocarbon group having from 1 to 18 carbon atoms which group may be olefinically unsaturated and/or contain an inert substituent; an aromatic hydrocarbon group having 6 to 18 carbon atoms and optionally containing an inert substituent; an araliphatic hydrocarbon group having 7 to 18 carbon atoms optionally containing an inert substituent; a cycloaliphatic hydrocarbon group having 5 to 18 carbon atoms optionally containing an inert substituent; an alkoxy group having 1 to 18 carbon atoms; or an aryloxy group having 6 to 18 carbon atoms;

X represents chlorine or bromine;

a represents an integer from 1 to 3;

b represents an integer from 1 to 3; and c represents an integer from 0 to 2 provided that the sum of a+b+c is equal to 4 comprising reacting a halogen silane corresponding to the general formula $$R_a SiX_{b+c}$$

with urea in a polar solvent at a temperature greater than or equal to 100° C. without application of pressure.

2. The process of claim 1 wherein the polar solvent is selected from the group consisting of sulfolane, organic acid amides which are liquid under the reaction conditions and mixtures thereof.

3. The process of claim 1 wherein the polar solvent is selected from the group consisting of sulfolane, dimethyl formamide, dimethyl acetamide, N-methylpyrrolidone, tetramethylurea, tetraethylurea and mixtures thereof.

4. The process of claim 1 wherein R represents a methyl group and X represents chlorine.

* * * * *